United States Patent
Estes et al.

(10) Patent No.: US 6,736,848 B2
(45) Date of Patent: May 18, 2004

(54) METHOD AND APPARATUS FOR USING FORMABLE POLYMERS FOR ORTHOPEDIC SUPPORT

(75) Inventors: Bradley T. Estes, Memphis, TN (US); John Elfstrom, Tucson, AZ (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/866,944

(22) Filed: May 29, 2001

(65) Prior Publication Data
US 2002/0180101 A1 Dec. 5, 2002

(51) Int. Cl.[7] ................................................ A61F 2/28
(52) U.S. Cl. ..................... 623/16.11; 623/919; 623/923
(58) Field of Search ........................... 606/53; 128/898; 623/901, 911, 919, 923, 16.11, 23.47, 23.51, 23.58, 23.61

(56) References Cited

U.S. PATENT DOCUMENTS

| | | | |
|---|---|---|---|
| 1,915,075 A | 6/1933 | Taylor | |
| 2,076,796 A | 4/1937 | Steinberger et al. | |
| 3,829,952 A | 8/1974 | Trask | 29/204 |
| 3,899,277 A | 8/1975 | Winter | 425/383 |
| 4,512,038 A | 4/1985 | Alexander et al. | 3/1.9 |
| 4,565,002 A | 1/1986 | Matsuo et al. | 29/623.4 |
| 4,645,503 A | 2/1987 | Lin et al. | 623/16 |
| 5,139,134 A | 8/1992 | Schenck | 198/780 |
| 5,571,207 A | 11/1996 | Houser | 623/27 |
| 5,676,699 A | 10/1997 | Gogolewski et al. | 623/16 |
| 5,863,297 A * | 1/1999 | Walter et al. | 623/17.18 |
| 5,868,746 A | 2/1999 | Sarver et al. | 606/69 |
| 5,919,234 A | 7/1999 | Lemperle et al. | 623/16 |
| 5,919,235 A | 7/1999 | Husson et al. | 623/17 |
| 5,954,744 A | 9/1999 | Phan et al. | 606/198 |
| 6,015,436 A | 1/2000 | Schönhöffer | 623/17 |
| 6,017,366 A | 1/2000 | Berman | 623/21 |
| 6,024,764 A | 2/2000 | Schroeppel | 623/1 |
| 6,090,996 A | 7/2000 | Li | 623/11 |
| 6,093,205 A | 7/2000 | McLeod et al. | 623/17 |
| 6,102,933 A | 8/2000 | Lee et al. | 606/209 |
| 6,197,143 B1 | 3/2001 | Bodnar | 156/218 |

FOREIGN PATENT DOCUMENTS

| | | | |
|---|---|---|---|
| DE | 19649086 | 8/1998 | |
| FR | 1454233 | 7/1966 | |
| FR | 2 718 634 | 10/1995 | A61F/2/08 |

OTHER PUBLICATIONS

"Macro Pore™," German Web p. 1; Oct. 13, 2000.
"MacroPore™ Protective Sheets," Web pp. 1–2; Oct. 13, 2000.
"MacroPore FX™," Web pp. 1–2; Oct. 13, 2000.
"Biomaterials: Body Parts of the Future," by Cheryl R. Blanchard, Ph.D., from SwRI Technology Today—"Biomaterials" web pp. 1–9.
"Synthetic Biodegradable Polymers as Medical Devices," by John C. Middleton and Arthur J. Tipton, from Synthetic Biodegradable Polymers as Medical Devices (MPB archive, Mar. 98) web pp. 1–17.

* cited by examiner

*Primary Examiner*—Corrine McDermott
*Assistant Examiner*—William H. Matthews
(74) *Attorney, Agent, or Firm*—Woodard, Emhardt, Moriarty, McNett & Henry LLP

(57) ABSTRACT

An orthopedic implant is formed from a sheet of moldable material such as a polymer or a bioresorbable material using an instrument. The material is heated above its glass transition temperature so that it can be formed into the desired shape of the implant. Then the material is cooled below its glass transition temperature to harden the material such that it retains the implant shape. During surgery, a surgeon can form implants to fit unique orthopedic applications by using instruments having various internal and external mold forms between which the sheet of moldable material can be rolled, wound, pressed or drawn.

13 Claims, 7 Drawing Sheets

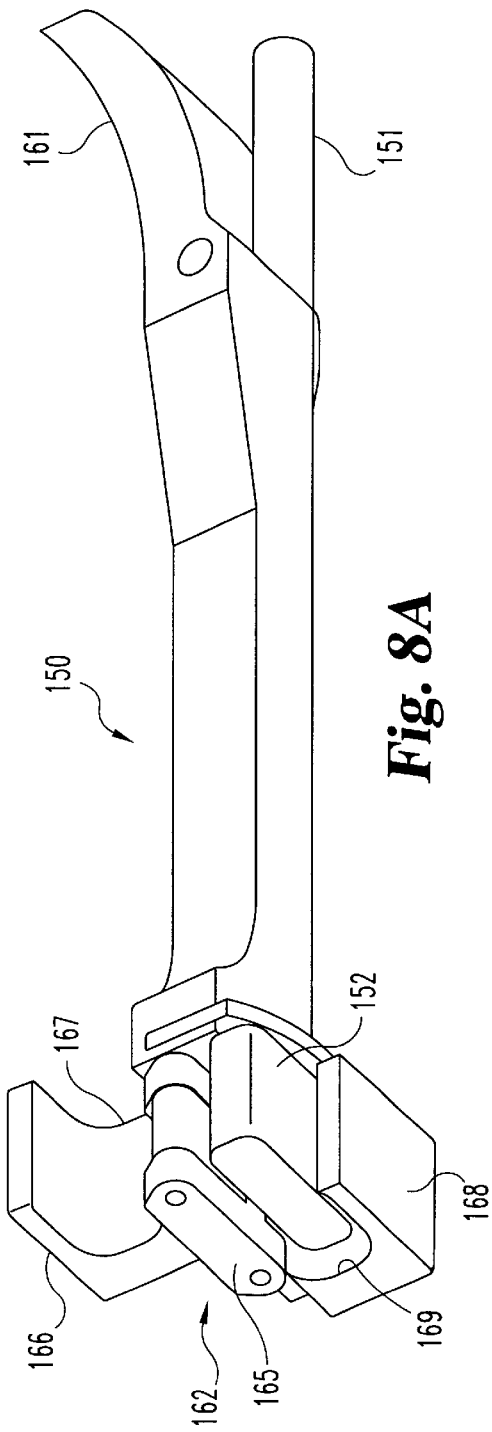
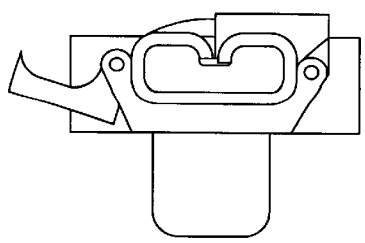
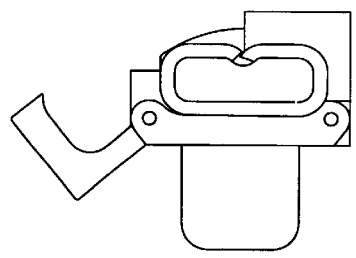
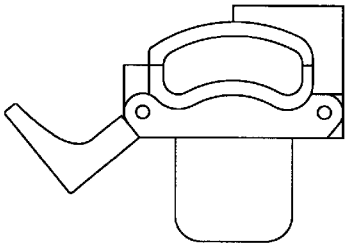
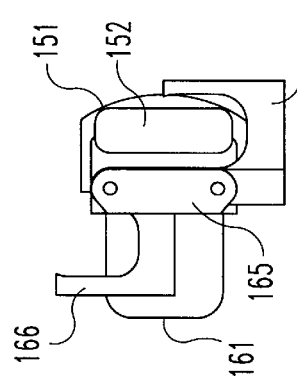

METHOD AND APPARATUS FOR USING FORMABLE POLYMERS FOR ORTHOPEDIC SUPPORT

BACKGROUND OF THE INVENTION

The present invention relates to orthopedic implants and to methods of making the same. More particularly, the present invention is directed to apparatus and methods of forming such implants from polymers and other resorbable materials during spinal or general orthopedic surgery.

Well known to those skilled in the art is the use of orthopedic implants to repair and treat bone defects, such as cracked and broken bones, as well as disorders of the skeletal system. Many of the orthopedic implants are formed primarily of metallic materials. Metallic implants have several disadvantages. First, a surgeon may not have at his disposal in the operating room an implant of the desired size and/or shape to fit the unique geometry of a patient's body. Additionally, metallic implants exhibit a significant compressive modulus over cortical bone and stress-shield new bone growth to induce osteoporosis and/or osteopenia, thereby resulting in cortical bone that is prone to refracture. Moreover, after repair of the bone defect, the implant is no longer needed; thus, removal of the implant necessitates a second surgery.

More recently, new treatment methods and improved materials, including nonmetallic implants, have been used to treat bone defects. Non-metallic implants can remain in the body, or alternatively, implants can be made of selected materials that biodegrade or are resorbable over a period of time ranging from a few days to several years. The absorption of bioresorbable medical implants into the body over a period of time allows bone growth in and around the space once occupied by the implant, thereby enabling repair of the bone at the defect site.

Known synthetic biodegradable polymers include homopolymers of lactic acid (PLA) and glycolic acid (PGA) and copolymers d, l, d/l lactic acid (PLDLA) and poly (lactide-co-glycolide) (PLA/PGA). A variety of these polymers are commercially available and can be synthesized to have a glass transition temperature between about 35° C. and about 65° C. These polymers become pliable when heated above their glass transition temperature and can be molded into a desired size and/or shape. Below the glass transition temperatures, they exhibit suitable compressive modulus to be used as orthopedic implants. Further, the compressive modulus and the rate of degradation can be tailored for specific medical applications by varying the ratio to d to l optical isomers of lactic acid in PLA and the ratio of lactic acid to glycolic acid in poly(lactide-co-glycolide).

In light of the above-described state of the art, the need exists for methods by which a surgeon, after assessing the particular geometry into which the implant must fit, can form the desired implant from a polymer or other resorbable material during the orthopedic surgery. The present invention satisfies this need in a novel and non-obvious way.

SUMMARY OF THE INVENTION

One aspect of the invention described herein is the ability of the surgeon to form a sheet of polymer or resorbable material in the shape of a spinal or general orthopedic implant in the operating room at the time of surgery.

One form of the present invention contemplates creating an orthopedic support from a sheet of moldable material such as a polymer or other resorbable material, including but not limited to PLA, PLDLA, PGA, and PGA/PLA. The surgeon assesses the geometry of the patient's body to determine the desired size and shape of the implant. The implant material is heated until it is above its glass transition temperature. The surgeon then forms it into the desired shape using an appropriate instrument and cools the material below its glass transition temperature. The material retains the desired shape.

Another form of the present invention contemplates a surgeon forming a moldable material into an orthopedic implant of a desired shape during surgery and positioning the implant in a patient to provide orthopedic support.

In another form, this invention provides apparatus for forming orthopedic implants from moldable material. Such apparatus enable the surgeon or operator to fashion implants specifically tailored to a patient's unique skeletal geometry. Implants fashioned according to such apparatus include shapes having, for example, circular, rounded-rectangular, kidney-shaped, semi-rectangular, crimped-rectangular, and B-shaped cross-sections.

One object of the present invention is to provide a unique method of forming, in the operating room and at the time of surgery, orthopedic implants from moldable material.

Further objects, features, and advantages of the present invention will be apparent from the description and drawings contained herein.

BRIEF DESCRIPTION OF THE DRAWINGS

FIG. 8A is perspective view of another embodiment of a tool to form a moldable implant according to the present invention.

FIG. 8B is a left end view of the tool in FIG. 8A.

FIG. 9 is a left end view of a tool to form a kidney-shaped implant according to the present invention.

FIG. 10 is a left end view of a tool to form a crimped-rectangular implant according to the present invention.

FIG. 11 is a left end view of a tool to form a B-shaped implant according to the present invention.

DESCRIPTION OF THE PREFERRED EMBODIMENTS

Figure 1:
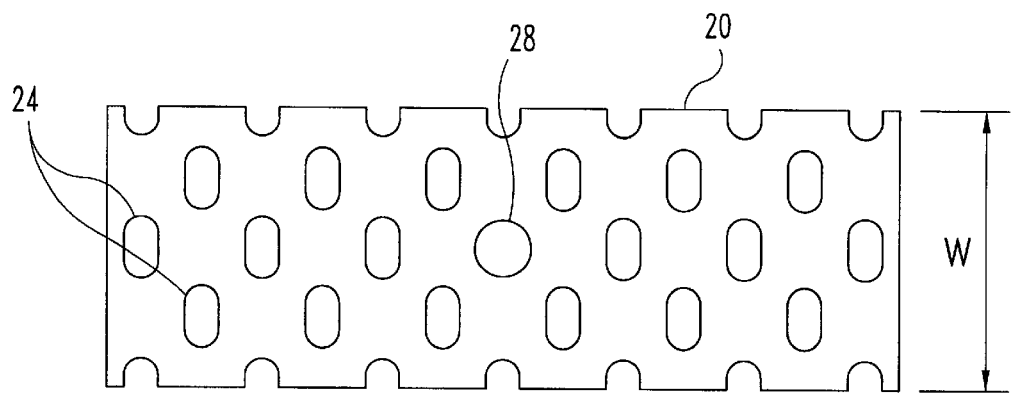
FIG. 1 is a plan view of a sheet of moldable material.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Illustrated in FIG. 1 is a sheet 20 of moldable material. The material can be a polymer or other moldable material. In the preferred embodiment, the material is a bioresorbable material, including, but not limited to PLA, PLDLA, PGA, or PGA/PLA. The moldable material is preferably characterized by its malleability when heated above its glass transition temperature and by its ability to remain in a deformed state when returned to a temperature below its glass transition temperature.

Figure 2:
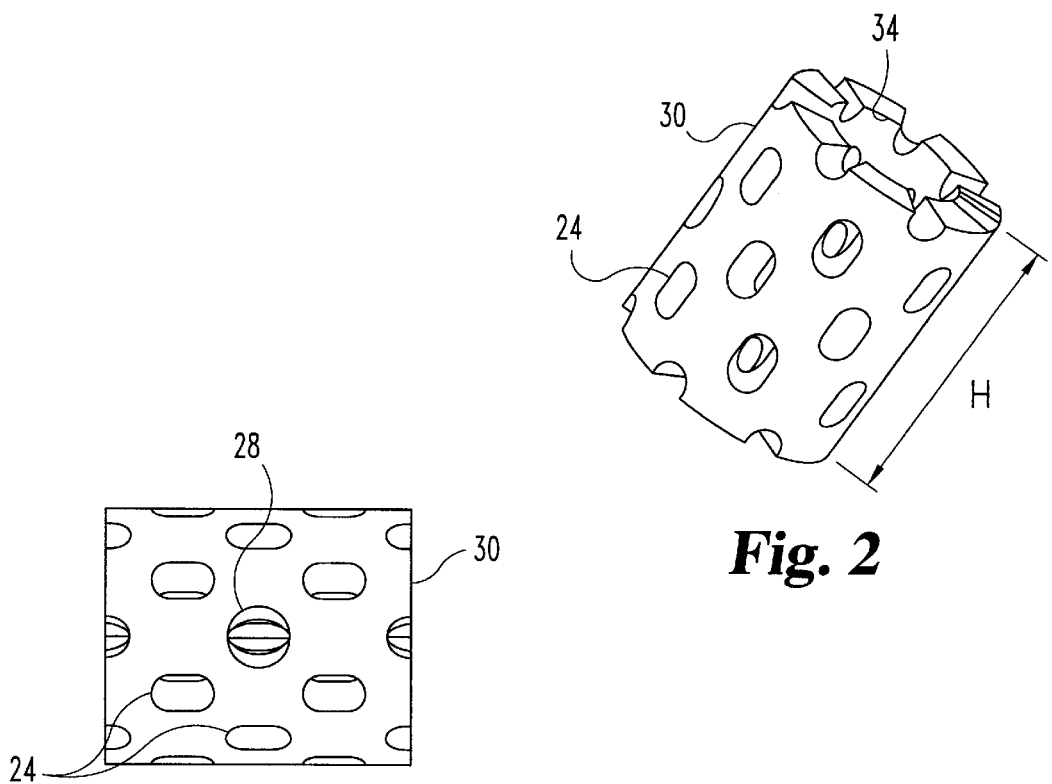
FIG. 2 is a perspective view of one embodiment of an implant formed from the moldable material of FIG. 1.
Figure 3:
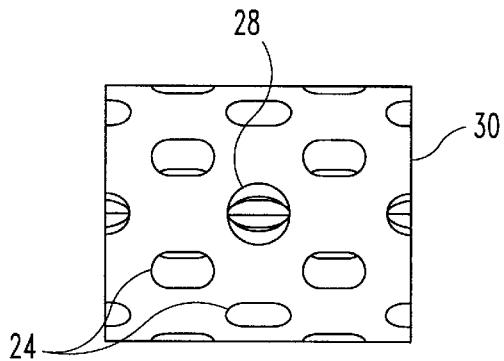
FIG. 3 is a side elevation view of the implant of FIG. 2.
Figure 4A:
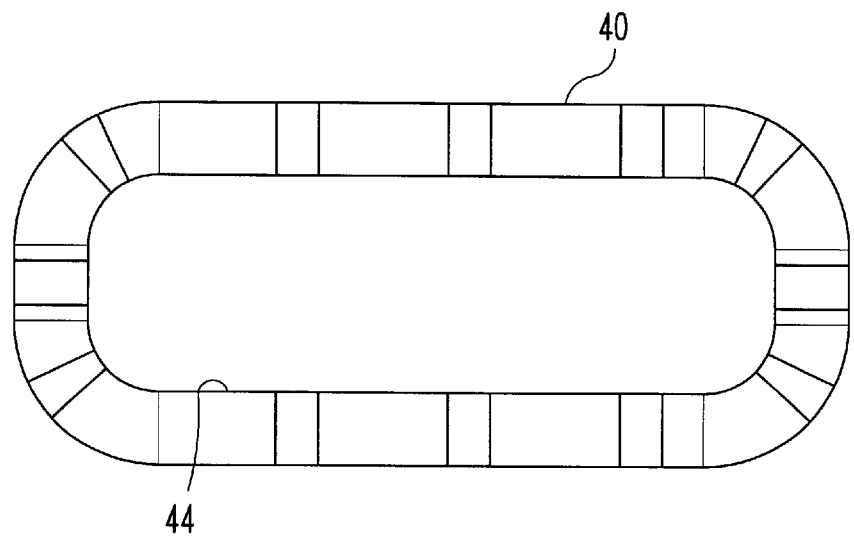
FIG. 4A is a top view of another embodiment of an implant formed from moldable material.
Figure 4B:
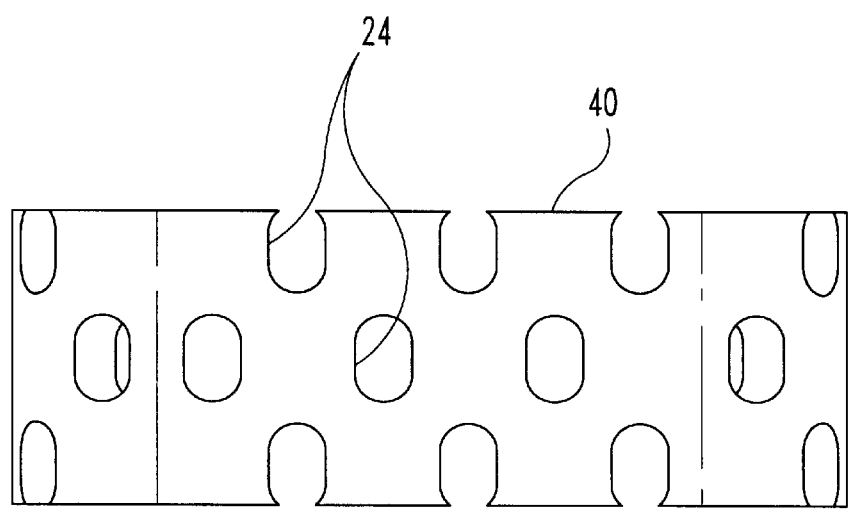
FIG. 4B is a side elevation view of the implant of FIG. 4A.

When heated above its glass transition temperature, the sheet of material in FIG. 1 can be formed or molded into cylindrical support or implant 30 shown in FIGS. 2 and 3. The geometrical configuration of the implant formed according to the present invention is not, however, limited to a cylinder. Rather, sheet 20 can be molded into any number of configurations including, but not limited to, rounded-rectangular implant 40 illustrated in FIGS. 4A and 4B, for example, as well as kidney-shaped, crimped-rectangular and B-shaped implants discussed below.

In order to encourage bone growth and repair at the implant site, hollow cores 34 and 44 of implants 30 and 40, respectively, can be packed with a bone growth inducing substance (not shown). Sheet 20 of moldable material can be porous with one or more holes therethrough. Sheet 20 is illustrated having a plurality of holes 24 therethrough such that, when an implant is formed and placed in the body, the presence of one or more holes 24 allows for the proliferation of tissue and vasculature from the region around the exterior of the implant, through holes 24, and to the bone growth inducing substance located in the core. Further, if the implant is formed from a bioresorbable material, then holes 24 create bridges of tissue, vasculature, and/or bone growth when the implant is reabsorbed, thereby providing structural support and allowing for the continued growth of tissue, vasculature and/or bone in the space previously occupied by the implant.

To facilitate insertion, circular hole 28, as best seen in FIGS. 1 and 3, may be provided in sheet 20 so that a tool (not shown) can be inserted therein to manipulate the implant into the desired position in the patient's body.

Several instruments for forming a sheet of moldable material into an orthopedic implant are discussed below. Such instruments are preferably made of metal in order to reduce wear and to minimize fatigue associated with the repeated temperature variations to which the instrument is subjected. Most preferably, the instrument is made of 17-4 PH stainless steel.

Figure 5A:
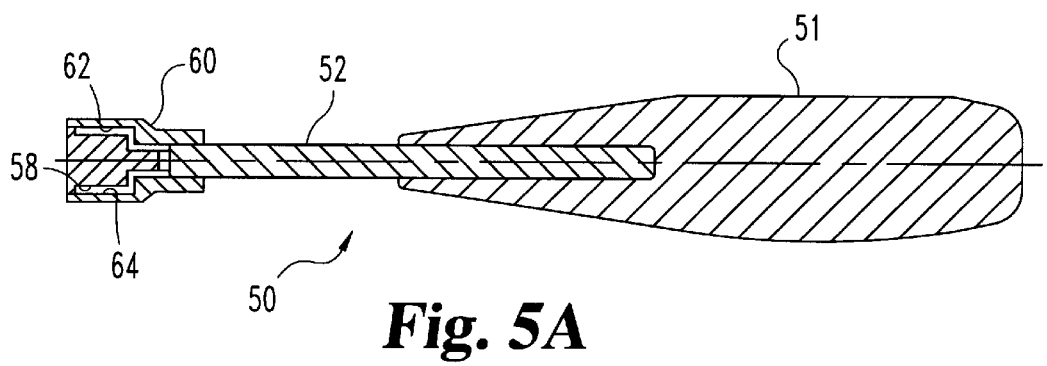
FIG. 5A is a cross-sectional view of one embodiment of a tool to form a moldable implant according to the present invention.
Figure 5B:
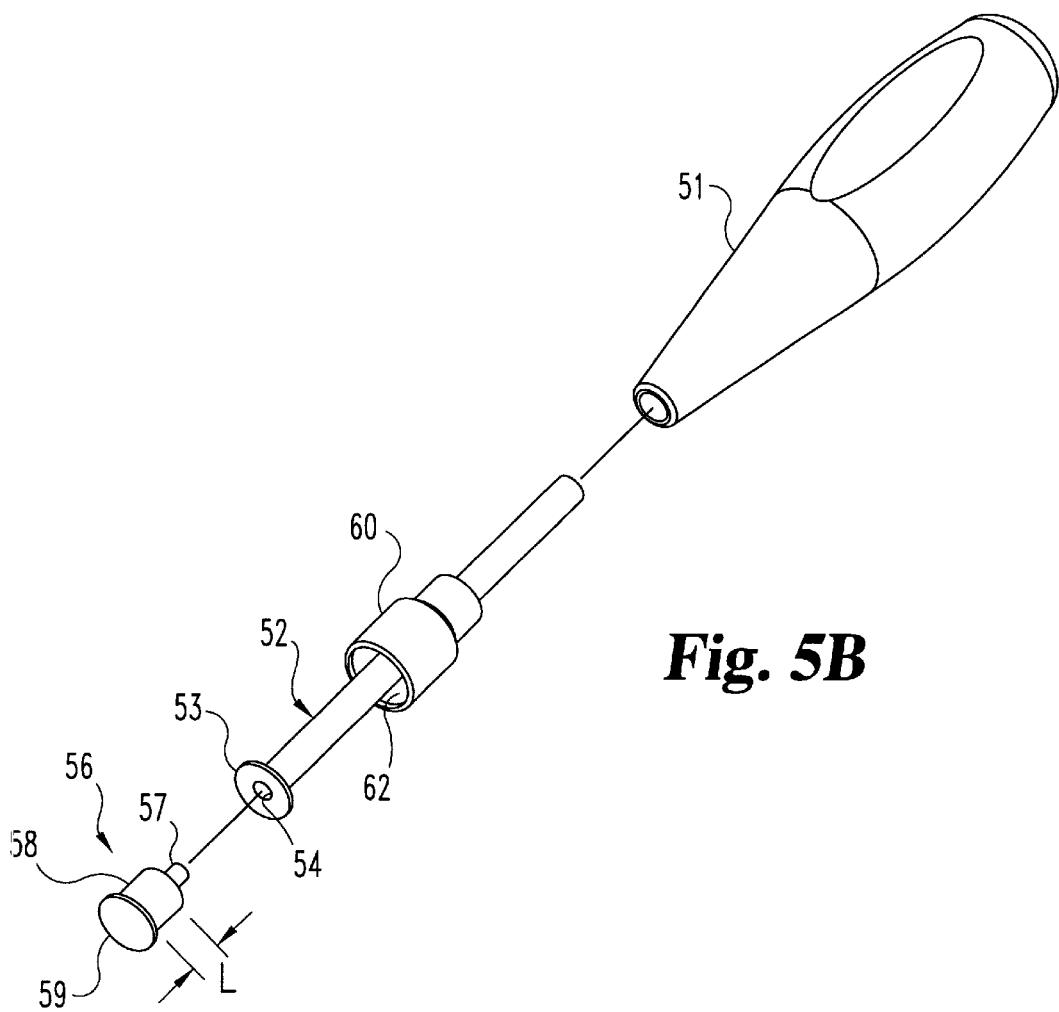
FIG. 5B is an exploded perspective view of the tool in FIG. 5A.

Instrument 50, illustrated in FIGS. 5A and 5B, is an apparatus used to form an orthopedic implant from sheet 20 of moldable material. Instrument 50 includes handle 51, shaft 52 detachably connected to handle 51, spindle 56, and collar 60 slidably mounted on shaft 52. The end of shaft 52 distal from handle 51 includes end plate 53, as well as lumen 54. Spindle 56 includes a first end 57, internal mold form 58, and end cap 59. Instrument 50 further includes means for coupling shaft 52 and spindle 56. Such means for coupling include, but are not limited to a friction fit or threaded engagement of first end 57 of spindle 56 with lumen 54 of shaft 52. Thus, coupled shaft 52 and spindle 56 act like a plunger that can draw internal mold form 58 into external mold form 62 of collar 60.

To form an implant using instrument 50, spindle 56 is coupled to shaft 52 which, with collar 60 mounted thereon, is connected to handle 51. A sheet of moldable material, for example sheet 20 shown in FIG. 1, is heated above glass transition temperature and wrapped around internal mold form 58 of spindle 56. Internal mold form 58 is inserted into external mold form 62 by moving collar 60 along shaft 52 until collar 60 abuts against end plate 53 as illustrated in FIG. 5A. The moldable material is located in recess 64 defined between internal mold form 58 of spindle 56 and external mold form 62 of collar 60 and between end cap 59 of spindle 56 and end plate 53 of shaft 52. External mold form 62 may be tapered to facilitate entry of the moldable material into collar 60, so that the material is pressed between the two forms 58 and 62. While the moldable material is held in position between internal and external mold forms 58 and 62, respectively, the temperature of the moldable material is lowered below its glass transition temperature in order to set or harden the material. The resulting implant is removed from instrument 50 by sliding collar 60 toward handle 51, uncoupling shaft 52 from spindle 56, and sliding the implant off of the proximal end of spindle 56.

Heating the sheet of moldable material above its glass transition temperature can readily be accomplished by submersing the sheet in a sterile warm-water bath, the temperature of which is above the glass transition temperature of the moldable material. Similarly, lowering the temperature of the moldable material below its glass transition temperature can be accomplished by submersing the distal end of instrument 50, with the sheet of moldable material formed therein, into a sterile cold-water bath, the temperature of which is below the glass transition temperature of the moldable material.

As can be readily appreciated from FIG. 5A, the internal diameter of the implant formed using instrument 50 is defined by the diameter of internal mold form 58 of spindle 56, and the external diameter is defined by the diameter of external form mold 62 of collar 60, so long as the thickness of the sheet of moldable material is great enough to span the thickness of recess 64. Thus, the internal and external diameters of an implant formed using instrument 50 can be varied by selecting a sheet of moldable material of the appropriate thickness and by selecting different combinations of spindles and collars with mold forms 58 and 62 having the desired diameters. Similarly, the height, H, of the implant (see FIG. 2) is governed by the width, W, of the sheet of moldable material (see FIG. 1), as well as the length, L, of internal mold form 58. Therefore, implants of various heights can be formed from appropriately dimensioned sheets of moldable material using instrument 50 by selecting spindles having an internal form mold of the appropriate length.

The detachable connection of shaft 52 and handle 51 permits collars having various external mold form diameters and lengths to be mounted on shaft 52. Also, spindles having various internal mold form diameters and lengths can be coupled to shaft 52. This interchangeability of variously-sized collars and spindles allows a surgeon to form an implant that is sized precisely to fit the geometry of each unique orthopedic application. Thus, a surgeon practicing the method of the present invention assesses the geometry of the implant site, selects the appropriately sized mold forms, proceeds according to the above methodology to form an implant of the desired size using instrument 50, removes the implant from the instrument, and then positions the implant in the patient to provide orthopedic support. Any of the steps of the method of the present invention may, but need not necessarily (with the exception of the last step), be performed in the operating room during surgery.

Figure 6A:
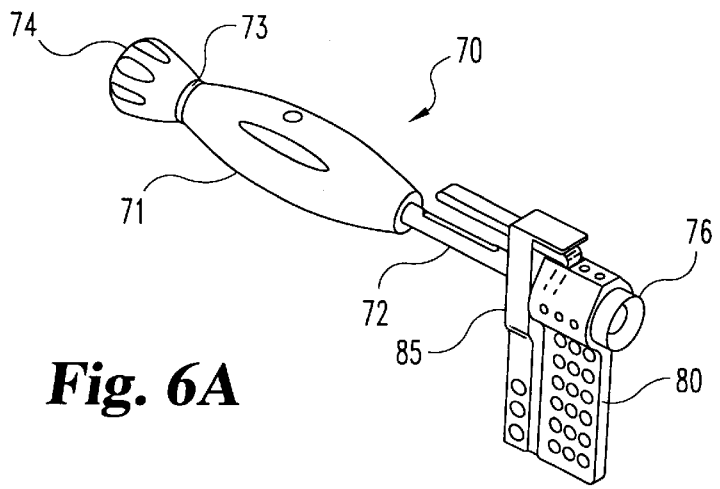
FIG. 6A is a perspective view of another embodiment of a tool to form a moldable implant according to the present invention.
Figure 6B:
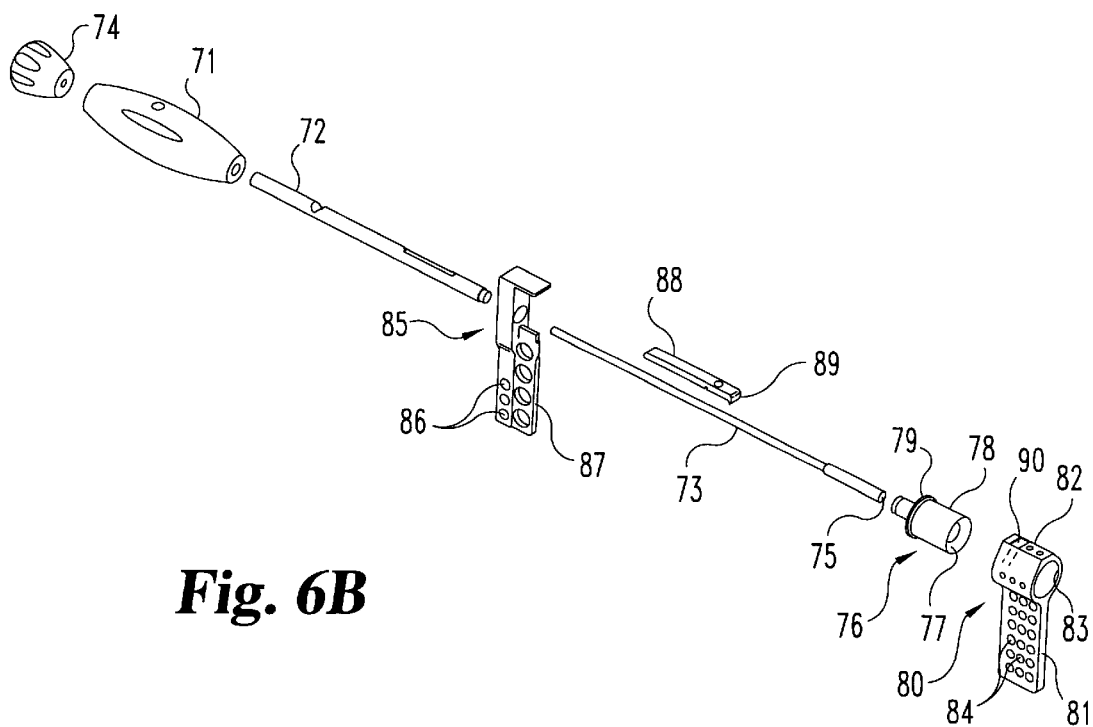
FIG. 6B is an exploded perspective view of the tool in FIG. 6A.

Another embodiment of an apparatus used to form an orthopedic implant from a sheet of moldable material is illustrated in FIGS. 6A and 6B as instrument 70. Instrument 70 includes shaft 72 having a lumen therethrough and mandrel 73 coaxial with shaft 72 and positioned within the lumen of shaft 72. Handle 71 is connected to the proximal end of shaft 72, and knob 74 is connected to the proximal end of mandrel 73 such that rotation of knob 74 with respect to handle 71 affects rotation of mandrel 73 with respect to shaft 72. Connected to the distal end of shaft 72 is base 85 for receiving sheet 87 of moldable material. Adjustment mechanism 88 connects to base 85 and includes tab 89 at its distal end.

The distal end of mandrel 73 includes keyway 75 that couples to and drives spindle 76. Spindle 76 includes drum 78 with slot 77 therein, as well as end plate 79. Drum 78 provides an internal mold form, and slot 77 is sized to receive sheet 87 therein and provides a means of anchoring sheet 87 to drum 78. Instrument 70 further includes guide 80 having chamber 81 for receiving sheet 87 and chamber 82 that provides an external mold form when sheet 87 is formed or rolled onto drum 78. When guide 80 is properly positioned, mold chamber 82 slides over spindle 76, and sheet chamber 81 receives sheet 87 that has been loaded into base 85. Tab 89 of adjustment mechanism 88 engages one of a plurality of grooves 90 on guide 80 in order to retain guide 80 stationary with respect to base 85 and to enable variation in the length of drum 78 contained within mold chamber 82 of guide 80.

To practice the method of the present invention using instrument 70, the surgeon selects sheet 87 of moldable material having the appropriate width, thickness, and length to yield the desired size of the implant. A spindle sized to accommodate the sheet of moldable material is connected to mandrel 73. Sheet 87 is then inserted into base 85 until the upper end of sheet 87 is received in slot 77 in drum 78. An appropriately sized guide 80 is selected such that the width of sheet 87 fits between end plate 79 of spindle 76 and end cap 83 of guide 80. Guide 80 is then placed over spindle 76 and held stationary with respect to base 85 by engagement of tab 89 into one of the plurality grooves 90 on guide 80. Thus positioned, chamber 81 of guide 80 receives sheet 87 therein, and spindle 76 is free to rotate within chamber 82 of guide 80.

In order to form sheet 87 into an implant, the temperature of the moldable material must be altered with respect to its glass transition temperature to permit deforming and then hardening of the material. As described above with respect to instrument 50, the distal end of instrument 70 can, for example, be submersed in sterile water baths to raise and lower the temperature of the material. Guide 80 and base 85 include holes 84 and 86, respectively, that permit the water to contact sheet 87 during submersion in a bath in order to better conduct temperature between the water and sheet 87. Further, holes 84 and 86 reduce the thermal mass of the distal end of instrument 70, thereby enabling a more efficient temperature change when instrument 70 is moved between water baths.

When sheet 87 of moldable material is warmed above its glass transition temperature, the rotation of knob 74 with respect to handle 71 causes mandrel 73 and spindle 76 driven by keyway 75 to rotate relative to base 85 and guide 80. The rotation of spindle 76 causes sheet 87, with its upper end received in slot 77, to be wound onto drum 78. Further, this rotation provides means for rolling sheet 87 between the internal mold form of drum 78 and the external mold form provided by chamber 82. The temperature of the moldable material is then lowered below its glass transition temperature in order to set or harden the material into the implant defined by the internal mold form of drum 78 and the external mold form of chamber 82.

The height of the implant resulting from the use of instrument 70 can be varied by selecting sheets of moldable material having various widths. The adjustment of tab 89 of adjustment mechanism 88 to engage various of the plurality of grooves 90 on guide 80 changes the distance along drum 78 between end plate 79 of spindle 76 and end cap 83 of guide 80, in order to accommodate sheets 87 of various widths. The dimensions of the resulting implant can be further varied by interchanging variously sized spindles and guides since the diameters of drum 78 and mold chamber 82, respectively, define the inner and outer diameters of the implant.

Figure 7A:
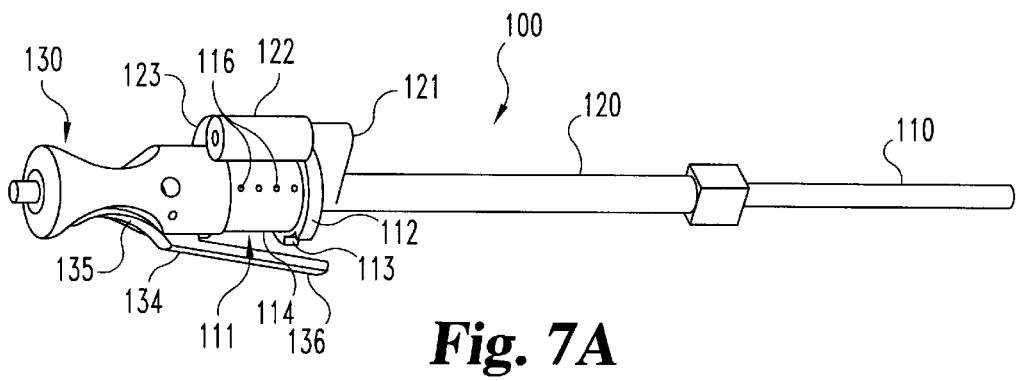
FIG. 7A is perspective view of another embodiment of a tool to form a moldable implant according to the present invention.
Figure 7B:
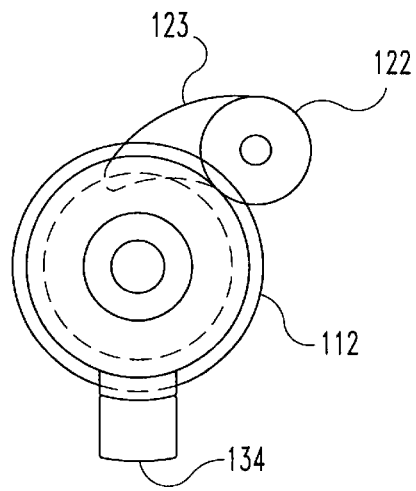
FIG. 7B is a left end view of the tool in FIG. 7A.

Another embodiment of an apparatus used in accordance with the present invention is instrument 100 shown in FIGS. 7A and 7B. Instrument 100 has an inner shaft 110 and an outer shaft 120 with a lumen therethrough. Inner shaft 110 is coaxial with, and rotatable with respect to, outer shaft 120. Inner shaft 110 is also slidable within the lumen of outer shaft 120. Attached to outer shaft 120 is offset arm 121 to which roller 122 with pressure guide 123 is connected. Additionally, attached to inner shaft 110 is spindle 111 having end plate 112 and internal mold form 114. End plate 112 abuts against, but is rotatable with respect to, offset arm 121. Instrument 100 further includes cap 130 appropriately sized to friction fit over the end of internal mold form 114 of spindle 111 opposite end plate 112. Moreover, cap 130 fits between internal mold form 114 and roller 122 such that the rotation of inner shaft 110 with respect to outer shaft 120 results in the rotation of the spindle/cap assembly with respect to the roller/pressure guide assembly.

Cap 130 also includes lever 134 with thumb mold 135 and arm 136. When a sheet of moldable material is wound onto internal mold form 114, arm 136 of lever 134 can be press fit into notch 113 of end plate 112 in order to hold the sheet on internal mold form 114. Arm 136 of lever 134 is particularly useful for anchoring an end of the sheet of moldable material against internal mold form 114 to retain the sheet on spindle 111, or for holding together the implant seam formed by the adjoining ends of the sheet moldable material, or for pressing an overlapping portion of the sheet of moldable material against internal mold form 114. When arm 136 is pressing into notch 113, thumb mold 135 of lever 134 protrudes radially away from cap 130. Thus, release of arm 136 from notch 113 is readily accomplished by pressing thumb mold 135 radially inward toward cap 130.

As discussed in conjunction with the formation of implants from a sheet of moldable material using instruments 50 and 70, the distal end of instrument 100, including cap 130 and spindle 111 along with roller 122 and pressure guide 123, can be submersed in sterile water baths in order to raise or lower the temperature of the moldable material in relation to its glass transition temperature. During submersion in a water bath, holes 116 in internal mold form 114 allow water to enter the interior of internal mold form 114, thereby facilitating conduction of the water temperature to the inner surface of the implant formed on internal mold form 114. Upon removal of instrument 100 from a water bath, the water flows out of the interior of internal mold form 114 through holes 116.

In the practice of the present invention using instrument 100, a sheet of moldable material is placed on internal mold form 114 and fed underneath roller 122. A means for winding the sheet on internal mold form 114 is provided by the rotation of outer shaft 120 with respect to inner shaft 110 which causes roller 122 and pressure guide 123 to act as external mold forms and move about the perimeter of internal mold form 114, thereby rolling the sheet of moldable material between the internal and external mold forms. Pressure guide 123 provides means for applying pressure to the moldable material to force it against internal mold form 114. Arm 136 of lever 134 can be pressed into notch 113 of end plate 112 to retain either one or both ends of the sheet of moldable material on internal mold form 114 during formation of the implant and during movement of instrument 100 between water baths.

Once formed on internal mold form 114, the implant is removed from instrument 100 by releasing arm 136 from notch 113 of end plate 112, removing cap 130 from the end of internal mold form 114, and disengaging roller 122 and pressure guide 123 from spindle 111 by sliding inner shaft 110 relative to outer shaft 120 to permit axial separation between spindle 111 and the roller/pressure guide assembly. The implant can then be easily slipped off of the end of internal mold form 114 opposite end plate 112.

As one of ordinary skill in the art will readily appreciate, the height of internal mold form 114 is preferably sufficient to accommodate the width of the sheet of moldable material. Further, the inner diameter of the implant formed using instrument 100 can be readily altered by interchanging spindles having internal mold forms of various diameters. Pressure guide 123 is biased to exert pressure against internal mold forms having a wide range of diameters.

FIG. 8A illustrates another embodiment of an apparatus used to form an orthopedic implant from a sheet of moldable material. Instrument 150 has first arm 151 and second arm 161 that is rotationally connected to first arm 151. Internal mold form 152 is connected to the distal end of first arm 151, and external mold form 162 is connected to the distal end of second arm 161. External mold form 162 further includes base 165, as well as first and second jaws 166 and 168, both of which are pivotally connected to base 165. FIGS. 8A and 8B show first jaw 166 in an open position and second jaw 168 in a closed position. First and second jaws 166 and 168 have inner contours 167 and 169, respectively. Internal and external mold forms 152 and 162 cooperate to form a rounded-rectangular implant such as that illustrated in FIGS. 4A and 4B.

The formation of an implant using instrument 150 is accomplished by opening first and second jaws 166 and 168 of external mold form 162. The rotation of second arm 161 with respect to first arm 151 in one direction causes external mold form 162 to separate or move away from internal mold form 152. A sheet of moldable material is inserted between internal mold form 152 and base 165 of external mold form 162. Reversing the rotation of second arm 161 so that it returns to its original position clamps or holds the sheet of moldable material under pressure between base 165 and internal mold form 152. Pivoting first and second jaws 166 and 168 to their closed positions causes inner contours 167 and 169 to engage the sheet of moldable material and press it against internal mold form 152 to create a rounded-rectangular implant. Thus, wrapping jaws 166 and 168 around the perimeter of internal mold form 152 further holds the sheet of moldable material under pressure between the mold forms defining the implant. The shape of the implant can be altered by using differently shaped internal and external mold forms 152 and 162. For example, FIGS. 9, 10, and 11 illustrate the mold forms of instruments that create kidney-shaped, crimped-rectangular, and B-shaped implants, respectively. Again with reference to FIG. 8A, opening jaws 166 and 168 and separating base 165 from internal mold form 152, by rotating second arm 161 with respect to first arm 151, allows the implant to be slipped off of internal mold form 152 and removed from instrument 150.

As discussed in connection with other embodiments of the present invention, the distal end of instrument 150 is submersed in sterile water baths having temperatures that alternately allow the sheet of moldable material to become malleable into a shape defined by the internal and external mold forms, and then allow the material to set or harden to form a rigid implant.

Figure 12A:
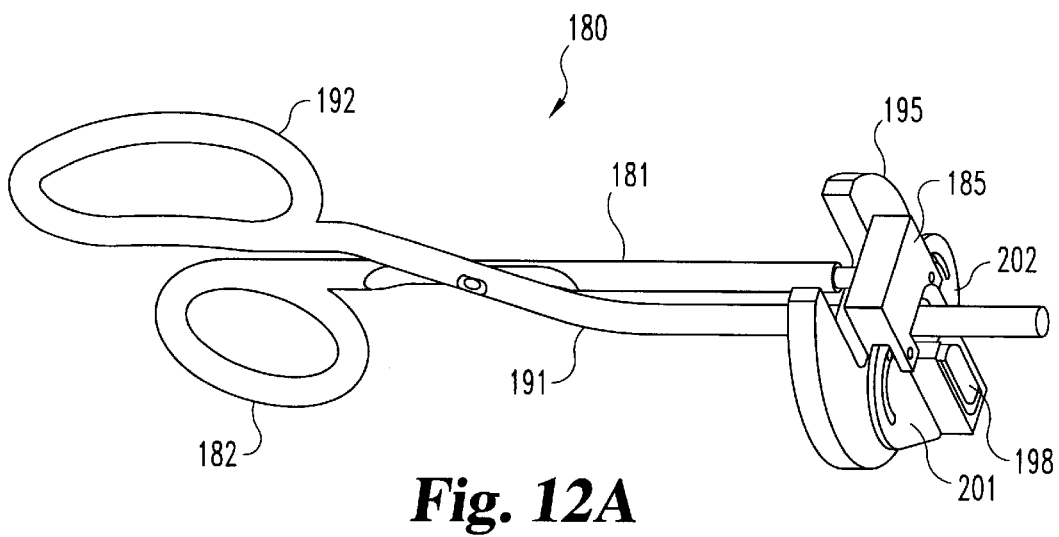
FIG. 12A is a perspective view of another embodiment of a tool to form a moldable implant according to the present invention.
Figure 12B:
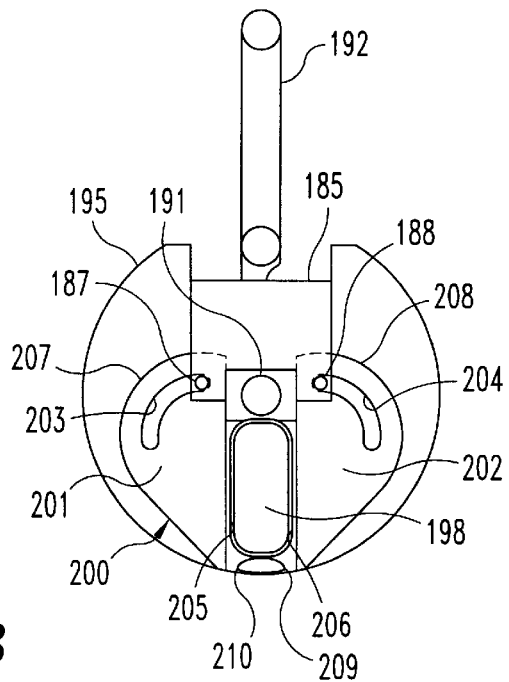
FIG. 12B is a right end view of the tool in FIG. 12A.

Yet another embodiment of an apparatus to form an orthopedic implant from a sheet of moldable material is shown in FIGS. 12A and 12B. Instrument 180 has first arm 181 and second arm 191 with finger loop 182 and thumb loop 192, respectively, at the proximal ends of the arms. Arms 181 and 191 are pivotally connected to affect a scissor actuation. Located at the distal end of the first arm 181 is block 185. Near the distal end of the second arm 191 are plate 195, clamshell 200, and inner mandrel 198 that forms an internal mold form for the orthopedic implant. Clamshell 200 has first and second arms 201 and 202 with first and second slots 203 and 204, respectively, therein. Also, first and second arms 201 and 202 have inner contours 205 and 206, respectively, and outer contours 207 and 208, respectively. First and second arms 201 and 202 of clamshell 200 are connected to block 185 via pins 187 and 188 slidably received in slots 203 and 204, respectively. As shown in FIGS. 12A and 12B, instrument 180 is in a closed position and clamshell 200 is closed about inner mandrel 198. When clamshell 200 is closed, tips 209 and 210 of clamshell arms 201 and 202, respectively, may fit flush against each other or may interdigitate as shown in FIGS. 12A and 12B.

To form an implant, instrument 180 is opened by displacing finger loop 182 and thumb loop 192 from each other. The resulting scissor actuation of first and second arms 181 and 191 causes the vertical displacement, as viewed in FIG. 12B, of block 185 from plate 195. Further, because block 185 is connected to first and second arms 201 and 202 of clamshell 200 via pins 187 and 188, the vertical displacement of block 185 causes pins 187 and 188 to slide within slots 203 and 204, respectively, thereby resulting in the cam actuation of first and second arms 201 and 202 and opening of clamshell 200.

As illustrated in FIG. 12B, slots 203 and 204 extend in a 90 degree quarter-circle such that the maximum displacement of block 185 pivots first and second arms 201 and 202 open each 90 degrees, thereby resulting in opening of clamshell 200 by 180 degrees. A person of skill in the art will readily appreciate that clamshell openings greater than or less than 180 degrees can be effected by altering the arc length of slots 203 and 204. However, for ease of insertion of the sheet of moldable material into instrument 180, clamshell 200 is preferably capable of opening 180 degrees or more.

The above-described scissor actuation of instrument 180 to open clamshell 200 causes displacement of inner contours 205 and 206 of first and second arms 201 and 202, respectively, away from inner mandrel 198. Thus, with clamshell 200 open 180 degrees or more, a sheet of moldable material is readily inserted edgewise between the top of inner mandrel 198 and inner contours 205 and 206. In order to retain the sheet in this location, block 185 may be lowered until inner contours 205 and 206 and/or tips 209 and 210 of clamshell arms 201 and 202, respectively, press the sheet against the top of inner mandrel 198. Alternatively inner mandrel may be spring biased to exert an upward pressure on the sheet of moldable material.

Heating the moldable material above its glass transition temperature, as, for example, by submersion of the distal end of instrument 180 in a warm water bath, permits the pressure exerted on the sheet by inner contours 205 and 206 of first and second arms 201 and 202, respectively, to deform the sheet and wrap or press it against the perimeter of inner mandrel 198 as finger loop 182 and thumb loop 192 are squeezed together and arms 201 and 202 of clamshell 200 are returned to their closed position. Closing arms 201 and 202 can be accomplished by either reversing the cam action of pins 187 and 188 in slots 203 and 204, respectively, or by pressing block 185 against outer contours 207 and 208 of clamshell arms 201 and 202, respectively. A person of skill in the art will appreciate that clamshell arms 201 and 202 of instrument 180 are functionally similar to jaws 166 and 168 of instrument 150.

Thus, positioned the sheet of moldable material is confined between inner contours 205 and 206, forming an external mold form, and inner mandrel 198, forming an internal mold form. Further, the edge of the sheet of moldable material is positioned against plate 195. To prevent out-of-plane twisting, an end cap (not shown) can be mounted on the distal end of the second arm 191 to press against the edge of the sheet opposite that positioned against plate 195. Once cooled below its glass transition temperature, the moldable material sets in the configuration defined by the internal and external mold forms, which, for those illustrated in FIGS. 12A and 12B result in a rounded-rectangular implant such as that illustrated in FIGS. 4A and 4B. The implant can be removed from instrument 180 by removing an end cap, if necessary, and by opening clamshell 200. With clamshell 200 open, inner contours 205 and 206 of arms 201 and 202, respectively, are displaced away from inner mandrel 198, thereby allowing the implant to be slipped off of the distal end of inner mandrel 198.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of using moldable material for orthopedic implants comprising:
    providing a sheet of moldable material said material having a glass transition temperature;
    heating said material above its glass transition temperature;
    using a mechanical instrument having an internal mold form and an external mold form to encircle said internal mold form and form said material into an implant of a desired shape;
    cooling said material below its glass transition temperature; and
    removing said material from the instrument prior to implantation into a patent.

2. The method of claim 1 further comprising the step of removing said implant from said instrument.

3. The method of claim 1 further comprising the step of positioning said implant to provide orthopedic support.

4. The method of claim 1 further comprising the step of selecting said moldable material from among PLA, PLDLA, PGA, PGAlPLA.

5. The method of claim 1, wherein said external mold form includes a pivoting jaw.

6. The method of claim 5, wherein the step of using said instrument comprises the step of pressing said sheet of moldable material between said internal and external mold forms.

7. The method of claim 5, wherein the step of using said instrument comprises the step of wrapping said external mold form around a perimeter of said internal mold form with said sheet of moldable material therebetween.

8. A method of preparing an implant, said method comprising:
    providing a sheet of moldable material, said material having a glass transition temperature;
    heating said material above its glass transition temperature;
    using an instrument having an internal mold form and an external mold form to bend said material and form said material into an implant of a desired shape having an internal cavity;
    removing said implant of a desired shape from said instrument; and
    cooling said material below its glass transition temperature.

9. The method of claim 8 wherein the instrument comprises a pivotally mounted external mold form.

10. The method of claim 9 comprising positioning the sheet of moldable material between the internal mold form and the external mold form and pivoting the external mold form to press the moldable material into a desired contour.

11. The method of claim 8 wherein the instrument is heated to a temperature level greater than the glass transition temperature of the moldable material.

12. The method of claim 8 wherein the external mold form comprises a base and a pair of jaws pivotally attached to said base.

13. The method of claim 8 wherein the moldable material is selected from the group consisting of: PLA, PLDLA, PGA, PGAlPLA, and mixtures thereof.

* * * * *